United States Patent
Shakespeare

(10) Patent No.: US 6,441,904 B1
(45) Date of Patent: Aug. 27, 2002

(54) METHOD AND APPARATUS FOR MEASURING PROPERTIES OF A MOVING FIBER WEB

(75) Inventor: John Shakespeare, Siuro (FI)

(73) Assignee: Metso Paper Automation Oy, Tampere (FI)

(*) Notice: Subject to any disclaimer, the term of this patent is extended or adjusted under 35 U.S.C. 154(b) by 0 days.

(21) Appl. No.: 09/262,701

(22) Filed: Mar. 4, 1999

(51) Int. Cl.$^7$ ................................. G01N 21/86
(52) U.S. Cl. ................ 356/429; 73/159; 162/198
(58) Field of Search ............... 356/429, 430, 356/431, 238.1, 238.2; 250/559.45, 559.46; 73/159; 162/198

(56) References Cited

U.S. PATENT DOCUMENTS

| | | | |
|---|---|---|---|
| 2,935,559 A | * 5/1960 | Dornier | 356/429 |
| 2,984,699 A | * 5/1961 | Dornier | 356/429 |
| 3,823,371 A | 7/1974 | Lippke | 162/263 |
| 4,055,077 A | 10/1977 | Loch | 73/73 |
| 4,319,847 A | 3/1982 | Howarth | 356/431 |
| 4,565,444 A | 1/1986 | Mactaggart | 356/73 |
| 4,903,528 A | 2/1990 | Balakrishnan | 73/159 |
| 5,047,652 A | 9/1991 | Lisnyansky | 250/571 |
| 5,110,218 A | * 5/1992 | Aizawa et al. | 374/153 |
| 5,212,452 A | 5/1993 | Mayer et al. | 324/662 |
| 5,379,652 A | * 1/1995 | Allonen | 73/862.55 |
| 6,341,522 B1 | * 1/2002 | Goss et al. | 73/159 |

FOREIGN PATENT DOCUMENTS

| | | | |
|---|---|---|---|
| SU | 458742 | * | 6/1975 |
| WO | 9951811 | | 10/1999 |

* cited by examiner

Primary Examiner—F. L. Evans
(74) Attorney, Agent, or Firm—Ladas & Parry

(57) ABSTRACT

The invention relates to a method and an apparatus for measuring properties of a moving web. Web properties are measured with a measuring apparatus where at least one sensor element is arranged to a rotating measuring roll. The measuring roll is in contact with the web to be measured, and the circumferential speed of the measuring roll is arranged to substantially equal the web speed, the web being substantially in non-slipping contact with the measuring roll for an arc of the rotation of the measuring roll.

22 Claims, 2 Drawing Sheets

METHOD AND APPARATUS FOR MEASURING PROPERTIES OF A MOVING FIBER WEB

Figure 1:
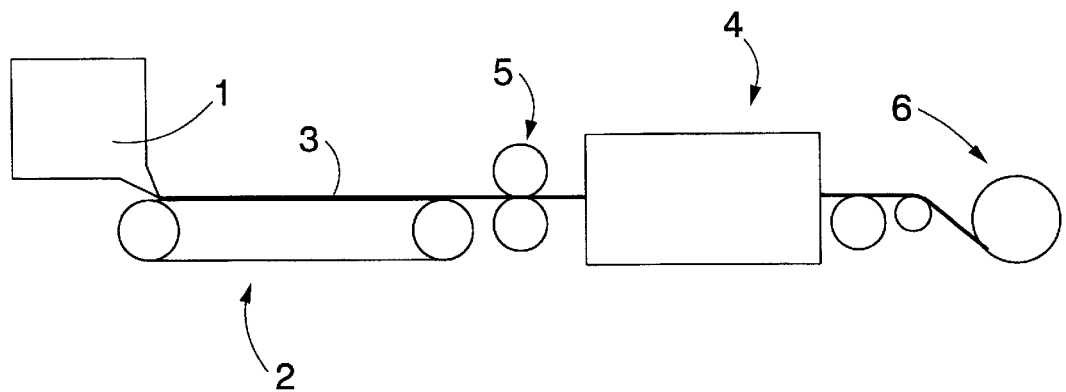

The invention relates to a method for measuring properties of a moving fiber web.

Further, the invention relates to an apparatus for measuring properties of a moving fiber web.

In the paper industry a traversing array of sensors is commonly used to measure properties of a moving fiber web during manufacture. The direction of traverse is normally substantially perpendicular to the direction of movement of the web. The sensors therefore measure properties of diagonal samples of the web, rather than the whole web. Typically, the speed of traverse is 20–40 centimeters per second, while the web moves at 10–30 meters per second. Measurements are made at substantially the same plurality of locations across the machine during each traverse, and may be made while traversing the web in one or both directions. The measurement from each such location is commonly termed a cell in the profile of measurements from a full traverse. Profiles measured in this way contain a combination of machine direction (MD) and cross-machine direction (CD) variations. Moreover, due to the scanning process, each CD location is infrequently sampled. Thus, scanning measurements provide only limited information about the MD and CD variability of the moving web. The method of measuring with scanning sensors requires that the web be unsupported in its passage through the scanning apparatus. Furthermore, since the traversing apparatus is stationary in the MD while the web may be moving at considerable speed, contact between the traversing sensors and the web is undesirable. As a result, the path of the web past the sensors may not be constant, and fluttering or other movement of the plane of the web relative to the sensors may compromise the accuracy of measurements, especially measurements of optical or surface properties of the web. This fluttering usually varies with web speed and other process operating conditions, and typically varies in degree across the web. Thus, the effect of web flutter on traversing measurements differs from time to time, and generally differs between the edges of the web and the centre of the web. A further disadvantage of this type of apparatus is the risk of web damage or breaks from contact between the moving fluttering web and the scanning sensors. In practice, such apparatuses can be utilized only in parts of the web manufacturing process where the web is sufficiently strong to support itself, and to survive occasional contact with the sensors due to fluttering. This prevents their use in, for example, the wet end of a paper machine.

The above mentioned technique employing traversing sensors is disclosed for example in U.S. Pat. No. 4,903,528 which further discloses methods which attempt to compensate for the diagonal path of the sensors relative to the web, and to estimate the web properties at locations in the web which were not measured. Such methods are of very limited efficacy, due to the incomplete representation of variation in web properties which is provided by traversing apparatus. In practice, the estimation is tolerably accurate only for wavelengths exceeding the MD web movement in a full CD traverse of the sensors. U.S. Pat. No. 4,319,847 discloses an apparatus which reduces the degree of sheet fluttering by employing directed jets to stabilize the web. This method reduces variation in the web path relative to the traversing sensors and thus can improve measurement accuracy for optical properties, but it does not completely eliminate web flutter. U.S. Pat. No. 5,047,652 discloses an alternative apparatus, comprising a backing roll which both stabilizes the web in a known constant curved path and provides optical standards for the traversing sensors.

Alternative techniques employ arrays of detectors deployed across the machine, measuring properties of the web at plural locations substantially simultaneously. Examples of such methods are disclosed in U.S. Pat. No. 4,565,444 including a variant method which employs multiple light pipes to a single detector. The technique disclosed in U.S. Pat. No. 4,565,444 overcome the drawbacks inherent in sequentially scanning across the web. However, they still scan the web in the MD, as the sensor apparatus remains stationary with respect to the moving web. The finite time constants of measurement devices cause the measurements to be an average of a significant length of the web in the MD, and this averaging time varies with the web speed. Typically, several milliseconds or dozens of milliseconds must be used for each measurement, during which time the web moves several dozens of centimeters. Thus, although the resolution of these measurement devices may be fixed and less than a centimeter in the CD, their resolution is dozens of centimeters and varying in the MD. Moreover, as the measurement device is stationary while the web is moving in the MD, contact between the apparatus and the web is undesirable. As a result, the above-mentioned problems of web flutter affect these measurement methods also. Similarly, as the web must also be unsupported in its passage through these apparatuses, they can be employed only where the web is sufficiently strong to support itself.

An object of the present invention is to provide a method and an apparatus which allow the above-mentioned drawbacks to be overcome.

The method of the invention is characterized by measuring the properties of the web with a sensor element which is arranged to a measuring roll which touches the web to be measured, wherein the circumferential speed of the measuring roll is arranged to substantially equal the web speed so that the web is substantially in non-slipping contact with the measuring roll.

Further, the apparatus of the invention is characterized by comprising at least one sensor element and a rotating measuring roll which touches the web to be measured, the sensor element being arranged to the measuring roll, wherein the circumferential speed of the measuring roll is arranged to substantially equal the web speed so that the web is substantially in non-slipping contact with the measuring roll.

The essential idea of the invention is that fiber web properties are measured with a measuring apparatus where at least one sensor element is arranged to a rotating roll which is in contact with the web to be measured, whereby the circumferential speed of the roll is arranged to substantially equal the web speed, the web being substantially in non-slipping contact with the roll. The idea of a preferred embodiment is that several sensor elements are arranged to the roll next to one another in the cross-machine direction. Furthermore, the idea of another preferred embodiment is that sensor elements are arranged to the roll one after another in the direction of its circumference, preferably in a regular grid pattern.

An advantage of the invention is that since the sensor element is continuously in contact with the same area of the web for the time sufficient for a reliable measurement, there is no MD averaging implicit in the measurement technique, except over the area of the sensor element. Further, when the spacing of sensor elements in the MD is fixed, the resolution of measurement in the MD is also fixed and does not vary with the web speed. The MD resolution is thus limited only by the dimensions of the sensor elements and high resolution may be easily achieved in MD measurements. When the measurements are made simultaneously at the plurality of CD locations, a true CD profile measurement is provided. Additionally, since the web is in contact with the roll, its position with respect to the sensors is known and constant, and does not vary either with CD position or with process operating conditions, so that web flutter does not affect the measurement technique. Further because the circumferential speed of the roll substantially equals the web speed the roll does not cause marks to the web or otherwise damage it. Yet another advantage is that the measuring roll can support the web during the measurement, so that the measuring apparatus can be situated in places where the web cannot support itself. For example, a measuring roll can be installed in the wet end of a paper machine.

Figure 2:
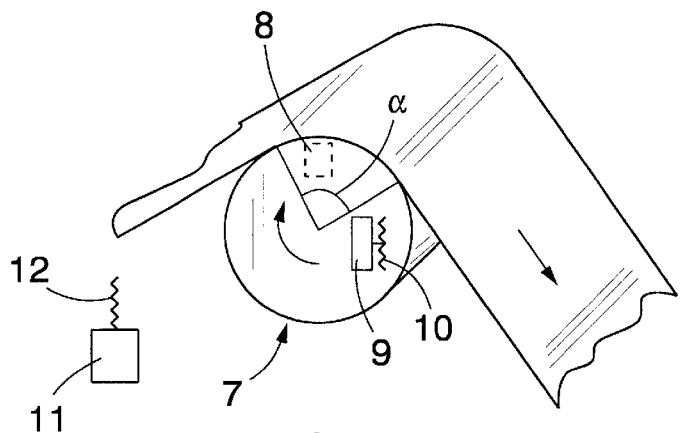
Figure 3:
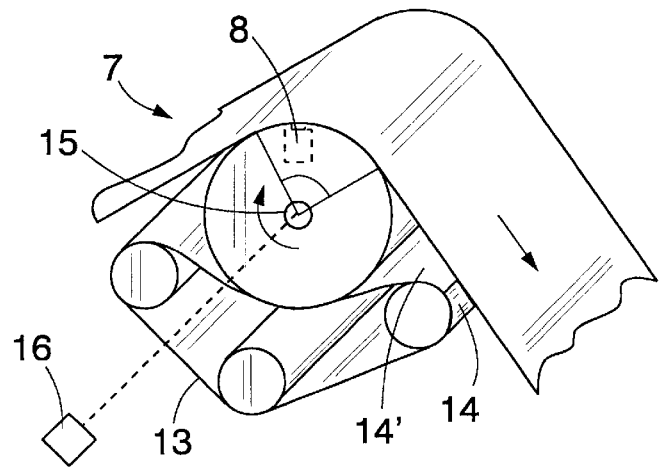
Figure 4A:
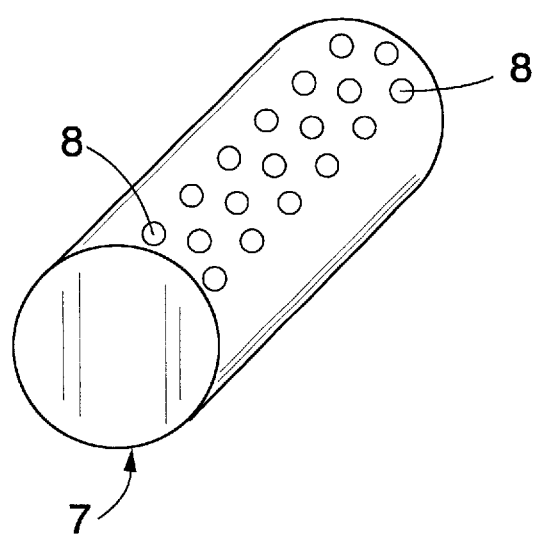
Figure 4B:
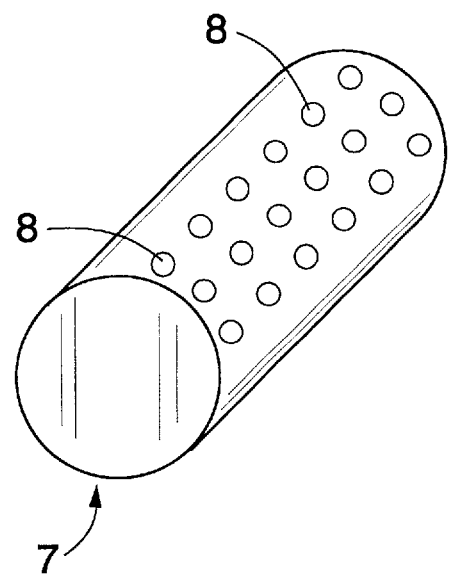

In the following, the invention will be described in greater detail with reference to the accompanying drawing, in which FIG. 1 is a schematic side view of a paper making process, FIG. 2 is a schematic view of an apparatus of the invention, FIG. 3 is a schematic view of another apparatus of the invention, and FIGS. 4a and 4b are schematic views of some roll arrangements used in connection with the apparatus of the invention.

FIG. 1 is a schematic side view of a paper machine. The paper machine comprises a headbox 1, from which pulp is fed into a former 2, where a fiber web 3 is formed of the pulp. The paper machine is used for manufacturing e.g. paper, paper board or tissue and consequently the fiber web 3 is a paper, paper board or tissue web. After the former 2 the fiber web 3 is led to a drying apparatus 4. A press 5 may be provided between the former 2 and the drying apparatus 4. After the drying apparatus 4 the fiber web is led to a reel 6. The paper machine may further comprise for example size presses, calender or coating units, which are not illustrated in the accompanying figure for the sake of clarity. Properties of the fiber web 3 may be measured at several locations of the paper machine using the measuring roll 7 of the invention.

FIG. 2 illustrates a measuring apparatus of the invention. A plurality of preferably substantially identical sensor elements 8 is deployed on the surface of the measuring roll 7. For the sake of clarity, only one sensor element 8 is shown in FIG. 2. The circumferential speed of the measuring roll substantially equals the web 3 speed whereby the moving web 3 is substantially in non-slipping contact with the measuring roll 7 for a portion of the rotation of the roll. Each sensor element 8 is continuously in contact with the same area of the web 3 for a finite time. A lower bound for that time can be determined from knowledge of the intended range of the web 3 speed and contact arc length. The contact arc length depends on the measuring roll's 7 diameter and contact arc angle α. The contact arc length can be chosen so that the exposure time exceeds the measurement time of the sensor elements 8. For example, a measuring roll of 1 metre diameter with a contact arc of 90 degrees provides an exposure time of 47 milliseconds at a web speed of 1000 metres per minute. As another example, a measuring roll of 1.5 metres diameter with a contact arc of 210 degrees provides an exposure time of 165 milliseconds at a web speed of 1000 metres per minute. Longer exposure times give more accurate measurements, or allow use of less expensive sensor elements. An economically optimal arrangement may be devised for a given measurement accuracy, by suitable choice of measuring roll diameter and sensor characteristics and price.

Each sensor element 8 is responsive to one or more properties of the web, and sensor elements 8 can be passive or active. A passive sensor element 8 contains at least one means of detection which is responsive to a directly sensible property of the web, such as surface temperature or surface electrostatic potential, or which is responsive to an externally applied stimulus which is modulated by the web in a way which depends on a property of the web. An active sensor element 8 contains at least one means of generating a stimulus and at least one means of detecting the modulation of that stimulus by the web. Measurement of web properties by active sensor elements 8 can be further enhanced by use of a suitably designed sheet used to support the web 3 while it is in contact with the measuring roll 7. Means of generating a stimulus need not coincide with means of detecting modulation of a stimulus either in number or deployment over the surface of the roll 7. With an active sensor element 8 the properties of the fiber web 3 can be measured accurately. Power can be supplied to the active sensor elements 8 for example by using direct electrical connection using brushes on the shaft of the roll, or on annuli at the end plate of the roll concentric with the shaft. Another option is magnetic induction in coils within the roll caused by the rotation of the roll so that the mechanical drive indirectly powers the electrical units within the roll. It is also possible to use self contained power within the roll using batteries or fuel cells which are replenished during shutdown.

A stimulus applied to the web 3, either by external means or by an active sensor element can be, for example, a mechanical or aerodynamical force or pressure, or can be a directional or diffuse polarized or unpolarized continuous or intermittent coherent or monochrome or polychrome radiant energy of fixed or variable spectral energy distribution in gamma, X-ray, ultraviolet, visible, infra-red, or radio bands, or can be a constant or variable electric or magnetic field, or bombardment with charged or uncharged particles such as neutrons, electrons, positrons, protons, alpha particles, or other ions. An externally applied stimulus can be provided by means proximal to the roll 7, or by means contained in a suitably devised enclosure for the roll 7, or by suitably constructed transporting sheet which accompanies the web while it is in contact with the roll 7.

The web 3 properties measured depend both on the nature of the stimulus, if any, and on the particular modulations of that stimulus to which the detector is responsive. For example, if the stimulating means of an active sensor element 8 illuminates the web directionally and perpendicularly to the roll 7 surface with polarized visible or near infra-red light whose polarization is varied during the time of contact between the web 3 and the sensor element 8, and its means of detection is responsive to the intensity of the reflected light, and the web 3 is accompanied by a reflective support sheet which is equally reflective at all planes of polarization, then the average response of the detector over all stimulus planes of polarization indicates the opacity of the web, while the variation in response at different stimulus planes of polarization indicates the distribution of fiber orientation within the sheet. As another example, if the stimulating means at one location on the roll 7 applies an alternating electric field to the web 3, and detecting means at nearby locations are responsive to electric field strength, then the average conductivity of the web may be measured along paths between stimulating and detecting means, indicating the local moisture content of the web 3. Multiple web 3 properties, such as moisture content and ash content, may be inferred from multiple measurements, such as conductivity and opacity, using multivariate calibration and modelling techniques such as multidimensional correlations, neural networks, or statistical factor analysis.

If required, means for calibrating the sensors can be provided as shown in FIG. 3. An endless standards sheet 13 moves in substantially non-slipping contact with the measuring roll 7 over a contact arc separate from the contact arc subtended by the moving web. The standards sheet 13 comprises one or more reference regions 14 of known properties and known responsiveness to various stimuli. The length of the standards sheet and the deployment of reference regions 14 on the standards sheet are preferably chosen so that each sensor element of the measuring roll comes into contact with those reference regions 14 which can be used to calibrate it. The response of each sensor element 8 to appropriate reference regions 14 of the standards sheet 13 can be used to calibrate individual sensor elements 8 to measure one or more properties of the web 3. For example, one reference region 14 of the standards sheet 13 could have a known low reflectivity at each band in a range of wavelengths, while another reference region 14' could have a known high reflectivity at each band in the same range of wavelengths, so that a sensor element for measuring reflectivity at one or more bands in that range of wavelengths can be calibrated from its response while in contact with each of these two regions. Responses of sensors of different types to each of plural reference regions, where plural properties are known for each reference region, can be used with multivariate calibration techniques such as those mentioned above to derive multivariate calibrations, and especially to derive multivariate calibrations for measuring properites which cannot be measured by individual sensor elements.

Data transmission between the measuring roll 7 and the data processing unit located outside it can be implemented in several different ways. For example, wires and slide brushes can be used for data transmission. Data transmission may also be implemented for example by arranging a narrow beam such as that produced by a laser or maser along the axis of rotation of the measuring roll 7 between a transceiver 15 within the measuring roll 7 and a transceiver 16 aligned outside the measuring roll 7, as depicted in FIG. 3. The laser beam acts as a link between, for example fiber optic devices inside and outside the measuring roll 7. Such beams may be at one or both ends of the measuring roll 7. Multiple frequencies may be combined and divided using commonly known methods into a single beam on the axis of rotation. Other narrow-beam communication methods which need not employ lasers or masers, such as modulation and detection of collimated incoherent polychrome visible or infra-red light, could also be used. However, data are preferably transmitted employing broad-beam or broadcast wireless technology, as depicted in FIG. 2. For example, the measuring roll 7 may be provided with a transceiver 9 to which data are collected from the sensor elements 8. The antenna 10 of the transceiver 9 transmits an electromagnetic signal to the antenna 12 of the transceiver 11 outside the measuring unit 7. The wireless datalink may be uni-directional or bidirectional with multiplexing etc. as options. Communication via the wireless datalink may employ amplitude or frequency or other modulation of an electromagnetic signal in the radio wave, micro-wave, or infra-red wavelength bands.

The sensor elements 8 are preferably deployed in a regular grid pattern on the surface of the measuring roll 7, such as a rectangular or hexagonal array or any other suitable regular grid pattern as shown in FIGS. 4a and 4b. For the sake of clarity FIGS. 4a and 4b illustrate only some of the sensor elements 8, but preferably there are sensor elements 8 on the whole circumference of the measuring roll 7. The grid spacings in the circumferencial (MD) and transverse (CD) axes of the measuring roll 7 need not be equal. Moreover, the grid spacings need not be uniform over the whole measuring roll 7. In particular the CD spacing may be closer in some parts of the roll 7 than others.

The drawings and the description relating thereto are intended merely to illustrate the inventive concept. In its details, the invention may be modified within the scope of the appended claims. For example, in alternative embodiments the sensor elements may be deployed in irregular patterns on the roll surface, or may be deployed over only a portion of the roll surface. The sensor elements on a roll need not all be responsive to the same web property, or may be differently responsive to more than one web property. Means of detection in a sensor element may be used in conjunction with means of stimulus for one or more other sensor elements to deduce different properties. The web can pass over plural measurement rolls sequentially, where sensor elements of different types are used on each roll, or where the sensor elements are arranged to come in to contact with different areas or opposite surfaces of the moving web. The measurement roll can be installed in a paper machine in any location where measurements of the web are needed. It can for example function as a turning roll, giving simultaneously measurement data of the web as depicted in FIGS. 2 and 3.

What is claimed is:

1. In a method for measuring properties of a moving fiber web, the improvements comprising:

applying a stimulus of mechanical or radiant energy to the fiber web, and measuring the properties of the fiber web, the fiber web being a paper web, paper board web or tissue web, with one or more sensor elements arranged to a measuring roll in contact with the fiber web by measuring at least partly the modulation of the stimulus by the fiber web, wherein a circumferential speed of rotation of the measuring roll is substantially equal to a speed of the moving of the fiber web so that the fiber web is substantially in non-slipping contact with the measuring roll for an arc of the rotation of the measuring roll.

2. A method according to claim 1, wherein at least one of the one or more sensor elements is an active sensor element for the applying of the stimulus.

3. A method according to claim 1, wherein the one or more sensor elements are arranged to the measuring roll next to one another in the cross-machine direction.

4. A method according to claim 3, wherein a true CD profile measurement is provided.

5. A method according to claim 1, wherein the one or more sensor elements are arranged to the measuring roll one after another in the circumferential direction of the measuring roll.

6. A method according to claim 1, wherein the one or more sensor elements are arranged to the measuring roll next to one another and one after another in a regular grid pattern.

7. A method according to claim 1, wherein the measuring roll is a turning roll.

8. A method according to claim 1, wherein measurement data collected by the one or more sensor elements are transmitted outside the measuring roll by wireless broad-beam datalink radio technology.

9. A method according to claim 1, wherein measuring data collected by the one or more sensor elements are transmitted outside the measuring roll by a wireless narrow-beam datalink along the axis of the measuring roll.

10. A method according to claim 1, wherein the speed of the moving of the fiber web makes the non-slipping contact with the measuring roll for the arc of the rotation of the measuring roll at least as long as a longest response time of the sensor elements.

11. In a method for measuring properties of a moving fiber web, the improvements comprising:

measuring the properties of the fiber web, the fiber web being a paper web, paper board web or tissue web, with one or more sensor elements arranged to a measuring roll in contact with the fiber web, wherein a circumferential speed of rotation of the measuring roll is substantially equal to a speed of the moving of the fiber web so that the fiber web is substantially in non-slipping contact with the measuring roll for an arc of the rotation of the measuring roll, and wherein the measuring roll also contacts an endless standards sheet moving in substantially non-slipping contact with the measuring roll, and wherein said standards sheet comprises at least one region wherein at least one of the properties is known and used to calibrate at least one of the one or more sensor elements.

12. A method according to claim 11, and further comprising:

applying a stimulus of mechanical or radiant energy to the fiber web, wherein the measuring is at least partly from modulation of the stimulus by the fiber web.

13. In an apparatus for measuring properties of a moving fiber web, the improvements comprising:

a stimulator for applying a stimulus of mechanical or radiant energy to the fiber web, one or more sensor elements and a measuring roll for rotation in contact with the fiber web, the fiber web being a paper web, paper board web or tissue web, the one or more sensor elements being arranged to the measuring roll and measuring the modulation of the stimulus by the fiber web, wherein a circumferential speed of the rotation of the measuring roll is substantially equal to a speed of the moving of the fiber web so that the fiber web is substantially in non-slipping contact with the measuring roll for an arc of the rotation of the measuring roll.

14. An apparatus according to claim 13, wherein the stimulator is at least one of the one or more sensor elements.

15. An apparatus according to claim 13, wherein the one or more sensor elements are arranged to the measuring roll next to one another in the cross-machine direction.

16. An apparatus according to claim 13, wherein the one or more sensor elements are arranged to the measuring roll one after another in the circumferential direction of the measuring roll.

17. An apparatus according to claim 13, wherein the one or more sensor elements are arranged to the measuring roll next to one another and one after another in a regular grid pattern.

18. An apparatus according to claim 13, wherein the measuring roll is a turning roll.

19. An apparatus according to claim 13, the apparatus comprising a transceiver arranged to the measuring roll and a transceiver arranged outside the measuring roll for transmitting and receiving measurement data collected by the one or-more sensor elements out of the measuring roll.

20. An apparatus according to claim 13, wherein the sensor elements are not television devices.

21. In an apparatus for measuring properties of a moving fiber web, the improvements comprising:

one or more sensor elements and a measuring roll for rotation in contact with the fiber web, the fiber web being a paper web, paper board web or tissue web, the one or more sensor elements being arranged to the measuring roll, and an endless standards sheet moving in substantially non-slipping contact with the measuring roll, and wherein said standards sheet comprises at least one region of known properties which is used to calibrate at least one of the one or more sensor elements, wherein a circumferential speed of the rotation of the measuring roll is substantially equal to a speed of the moving of the fiber web so that the fiber web is substantially in non-slipping contact with the measuring roll for an arc of the rotation of the measuring roll.

22. The apparatus according to claim 21, and further comprising:

a stimulator for applying a stimulus of mechanical or radiant energy to the fiber web, wherein one or more of the sensor elements measure for at least one of the properties from modulation of the stimulus by the fiber web.

* * * * *